United States Patent [19]

Machida et al.

[11] Patent Number: 4,929,612
[45] Date of Patent: May 29, 1990

[54] THIADIAZOLYLACETAMIDE CEPHEM DERIVATIVES

[75] Inventors: Yoshimasa Machida; Shigeto Negi; Takashi Kamiya; Yuuki Komatu; Isao Sugiyama; Yasunobu Kai, all of Ibaraki; Takaharu Nakamura, Chiba; Toshihiko Naito, Ibaraki; Kyosuke Kitoh, Ibaraki; Kanemasa Katsu, Ibaraki; Hiroshi Yamauchi, Ibaraki, all of Japan

[73] Assignee: Eisai Co., Ltd., Tokyo, Japan

[21] Appl. No.: 181,427

[22] Filed: Apr. 14, 1988

[30] Foreign Application Priority Data

Apr. 17, 1987 [JP] Japan .................................. 62-93234

[51] Int. Cl.$^5$ ................... C07D 501/46; A61K 31/545
[52] U.S. Cl. ..................................... 514/202; 540/222; 540/225
[58] Field of Search ................. 540/222, 227; 514/202

[56] References Cited

U.S. PATENT DOCUMENTS 4,486,586 12/1984 Takaya et al. ....................... 540/222
4,698,337 10/1987 Takaya et al. ....................... 540/222

FOREIGN PATENT DOCUMENTS 0188255 7/1986 European Pat. Off. .
58-04789 11/1983 Japan .
59-130295 7/1984 Japan .
60-97983 5/1985 Japan .

Primary Examiner—Nicholas S. Rizzo
Attorney, Agent, or Firm—Wenderoth, Lind & Ponack

[57] ABSTRACT

Novel thiadiazolylacetamide cephem derivatives of the following formula are described.

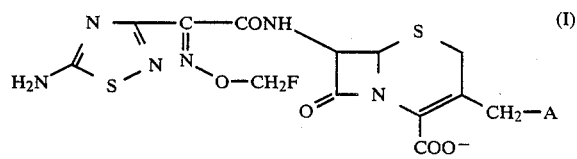

wherein A represents a quaternary ammonio group; or a pharmaceutically acceptable salt thereof. These novel compounds are useful as antibacterial agents, because they have a broad antibacterial spectrum ranging from gram-negative bacteria to gram-positive bacteria. Processes for the preparation of these novel compounds are also described.

5 Claims, No Drawings

THIADIAZOLYLACETAMIDE CEPHEM DERIVATIVES

BACKGROUND OF THE INVENTION

1) Field of the Invention:

This invention relates to novel cephem derivatives useful as antibacterial agents.

2) Description of the Related Art:

Many cephem derivatives having a 2-(5-amino-1,2,4-thiadiazol-3-yl)-2-methoxyiminoacetamido group at the 7-position and a quaternary ammoniomethyl group at the 3-position have been known to date. For example, see Japanese Patent Application Laid-Open Nos. 4789/1983, 130295/1984 and 97983/1985, European Patent Publication No. 188255 A2, etc.

Summary of the Invention

The present inventors have found that cephem derivatives having a 2-(5-amino-1,2,4-thiadiazol-3-yl)-2-fluoromethoxyiminoacetamido group at the 7-position and a quaternary ammoniomethyl group at the 3-position have excellent antibacterial activities, leading to completion of the present invention.

An object of this invention is therefore to provide novel compounds useful as antibacterial agents, a process for the preparation of the same compounds, and antibacterial agents containing the same compounds.

In one aspect of this invention, there is thus provided a thiadiazolylacetamidocephem derivative of the formula:

$$\text{(I)}$$

wherein A represents a quaternary ammonio group, or a pharamaceutically acceptable salt thereof.

In another aspect of this invention, there is also provided a process for the preparation of the thiadiazolylacetamidocephem derivative or the pharmaceutically acceptable salt thereof, which comprises reacting a compound of the formula:

$$\text{(II)}$$

wherein X represents a halogen atom or acetoxy group, a compound wherein the carboxyl and/or the amino groups(s) of the compound (II) is/are protected with protecting group(s), or a salt of the compound (II) or the protected compound, with a compound of the formula:

$$A' \qquad \text{(III)}$$

wherein A' represents an amine corresponding to the above-mentioned A, or a salt thereof, and if necessary removing the protecting group(s).

In a further aspect of this invention, there is also provided a process for the preparation of the thiadiazolylacetamidocephem derivative or the pharmaceutically acceptable salt thereof, which comprises reacting a compound of the formula:

$$\text{(IV)}$$

wherein A has the same meaning as defined above, a compound wherein the $-COO^-$ is protected with a protecting group, or a salt of the compound (IV) or the protected compound, with a compound of the formula:

$$\text{(V)}$$

a compound wherein the amino group is protected with a protecting group, a reactive derivative wherein the carboxyl group is substituted with a reactive group, or a salt of the compound (V), the protected compound, or the derivative; and if necessary, removing the protecting group.

The compounds of this invention have a broad antibacterial activity ranging from gram-negative bacteria to gram-positive bacteria.

The above and other objects, features and advantages of the present invention will become apparent from the following description of the invention and the appended claims.

DETAILED DESCRIPTION OF THE INVENTION AND PREFERRED EMBODIMENTS

The quaternary ammonio group A in the formula (I) may be either a cyclic quaternary ammonio group or an acyclic quaternary ammonio group. As exemplary acyclic quaternary ammonio groups, the following groups may be mentioned:

$$-\overset{+}{\underset{R_2}{\underset{|}{N}}}-R_3$$

wherein $R_1$, $R_2$ and $R_3$ may be the same or different and represent individually a lower alkyl, hydroxy lower alkyl or carbamoyl lower alkyl group.

As exemplary cyclic quaternary ammonio groups, the following groups may be mentioned:

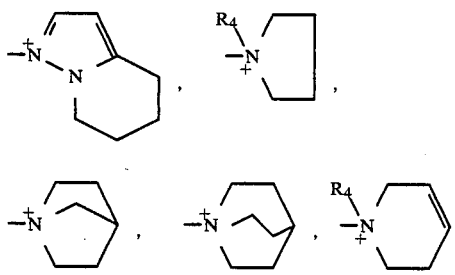

wherein $R_4$ represents a lower alkyl group. These cyclic quaternary ammonio groups may be substituted by any one of the group selected from a lower alkyl group, a hydroxy lower alkyl group, hydroxyl group or carbamoyl group.

Illustrative examples of the lower alkyl groups and the lower alkyl moieties in the substituted lower alkyl groups, which are represented by $R_1$–$R_4$ respectively, may include $C_1$–$C_4$ alkyl groups such as methyl, ethyl, n-propyl, i-propyl, n-butyl, sec-butyl and t-butyl.

As pharmaceutically acceptable salts of the compound of the formula (I), may be mentioned medicinally-acceptable salts, for example, inorganic acid salts such as hydrochloride, hydrobromide, hydroiodide, sulfate, carbonate and bicarbonate; organic carboxylates such as acetate, maleate, lactate, tartrate, aspartate, glutamate, serine salt and glycine salt; organic sulfonates such as methanesulfonate, hydroxymethanesulfonate, hydroxyethanesulfonate, taurine salt, benzenesulfonate and toluenesulfonate; etc.

Each of the compounds of the formula (I), which pertain to the present invention, has its syn-isomer (Z) and anti-isomer (E) with respect to its stereoscopic configuration at the following moiety:

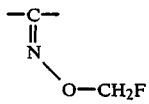

Although both isomers are included in the present invention, the syn-isomers are desired owing to their antibacterial activities.

The compounds of this invention can be produced by the following process.

The compounds of the formula (I) and their pharmaceutically acceptable salts can each be obtained by reacting a compound of the formula:

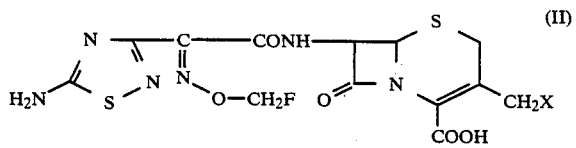

wherein X represents a halogen atom or acetoxy group, a compound wherein the carboxyl and/or the amino group(s) of the compound (II) is/are protected with protecting group(s), or a salt of the compound (II) or the protected compound, with a compound of the formula:

A'                           (III)

wherein A' represents an amine corresponding to the above-mentioned A, or a salt thereof, and if necessary removing the protecting group(s).

As the halogen atom X in the formula (II), may be mentioned an iodine, bromine or chlorine atom.

Where X is an acetoxy group in the above reaction, it is desirable to conduct the reaction at a reaction temperature of 30° C.–90° C. in the presence of an alkali metal salt. As the alkali metal salt, there are mentioned sodium iodide, potassium iodide, sodium bromide, potassium bromide, potassium thiocyanate, sodium thiocyanate, sodium nitrate, potassium nitrate or the like. It is possible to use, as a reaction solvent, an aqueous solvent such as water or buffer, a hydrophilic solvent such as formamide, tetrahydrofuran, methanol, dimethylformamide, acetonitrile or dioxane, or a mixed solvent thereof.

Where X stands for a halogen atom, the above reaction can be carried out at a reaction temperature of −10° C.—+60° C., preferably, 0° C.—+40° C. A dry organic solvent is preferred as a reaction solvent. Illustrative examples of the usable organic solvent may include lower alkyl nitriles such as acetonitrile and propionitrile; lower alkyl halides such as chloromethane, dichloromethane and chloroform; ethers such as dioxane and ethyl ether; amides such as dimethylformamide; esters such as ethyl acetate; ketones such as acetone; hydrocarbons such as benzene; alcohols such as methanol and ethanol; sulfoxides such as dimethylsulfoxide; and mixed solvents thereof.

The removal of the protecting group(s) may be effected by a usual method such as hydrolysis or reduction, depending on the kind(s) of the protecting group(s) used.

As protecting groups for the amino groups and carboxyl groups in the salt of the compound of the formula (II), the salt of the compound of the formula (III) and the compound of the formula (II), any routine protecting groups may be used so long as the above reaction is not impaired.

As illustrative examples of the protecting group for each amino group, may be mentioned formyl, acetyl, chloroacetyl, dichloroacetyl, phenylacetyl, thienylacetyl, t-butoxycarbonyl, benzyloxycarbonyl, trityl, p-methoxybenzyl, diphenylmethyl, benzylidene, p-nitrobenzylidene and m-chlorobenzylidene groups. Illustrative examples of the protecting group for each carboxyl group may include p-methoxybenzyl, p-nitrobenzyl, t-butyl, methyl, 2,2,2-trichloroethyl, diphenylmethyl and pivaloyloxymethyl groups. Use of a silylating agent such as N,O-bis(trimethylsilyl)acetamide, N-methyl-N-(trimethylsilyl)acetamide, N-methyl-N-(trimethylsilyl)trifluoroacetamide or N-(trimethylsilyl)acetamide is convenient, since it can protect both amino and carboxyl groups at the same time.

The salt of the compound of the formula (II) and the salt of the compound for the formula (III) may be chosen suitably depending on their functional groups, for example, from salts such as alkali metal salts such as sodium and potassium salts; alkaline earth metal salts such as calcium and magnesium salts; ammonium salts; quaternary ammonium salts such as triethylammonium and betaine salts; inorganic acid salts such as hydrochlorides, hydrobromides, sulfates, carbonates, hydroiodides and bicarbonates; organic carboxylates such as acetates, trifluoroacetates, maleates, lactates and tartrates; organic sulfonates such as methanesulfonates, hydroxymethanesulfonates, hydroxyethanesulfonates, taurine salts, benzenesulfonates and toluenesulfonates;

amine salts such as trimethylamine salts, triethylamine salts, pyridine salts, procaine salts, picolinate, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; and amino acid salts such as arginine salts, aspartates, lysine salts, glutamates, serine salts and glycine salts.

The compounds of this invention may also be prepared by the following process.

The compounds of the formula (I) and their pharmaceutically acceptable salts can each be obtained by reacting a compound of the formula:

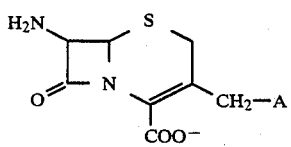

wherein A has the same meaning as defined above, a compound wherein the —COO⁻ is protected with a protecting group, or a salt of the compound (IV) or the protected compound, with a compound of the formula:

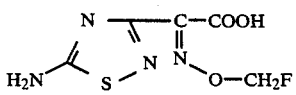

a compound wherein the amino group is protected with a protecting group, a reactive derivative wherein the carboxyl group is substituted with a reactive group, or a salt of the compound (V), the protected compondd, or the derivative; and if necessary, removing the protecting group.

The above process may be carried out under conditions for usual N-acylation reactions. For example, the reaction may be effected at $-50°$ C.$-+50°$ C., preferably, $-20°$ C.$-+30°$ C. in the presence or absence of a base in an inert solvent. As exemplary inert solvents, may be mentioned acetone, tetrahydrofuran, N,N-dimethylformamide, N,N'-dimethylacetamide, dioxane, dichloromethane, chloroform, benzene, toluene and acetonitrile as well as mixed solvents thereof. Illustrative examples of the base may include N,N-dimethylaniline, triethylamine, pyridine, N-methylmorpholine, etc.

Where a carboxylic acid (—COOH) represented by formula (V) is used in the process of this invention, it is desirable to conduct the reaction in the presence of a condensing agent such as N,N'-dicyclohexylcarbodiimide, N,N'-diethylcarbodiimide, N-cyclohexyl-N'-morpholinoethylcarbodiimide, trialkyl phosphites, ethyl polyphosphates or p-toluenesulfonic acid chloride. Where a reactive derivative of the formula (V) in which the carboxyl group has been substituted by a reactive group is used, illustrative examples of the reactive derivative may include acid halides such as the acid chloride and acid bromide; the corresponding acid anhydride; mixed acid anhydrides with carboxylic acids such as ethyl chlorocarbonate, trimethylacetic acid, thioacetic acid and diphenylacetic acid; active esters with 2-mercaptopyridine, cyanomethanol, p-nitrophenol, 2,4-dinitrophenol and pentachlorophenol; active acid amides with saccharin and the like; etc.

As the protecting group for the —COO⁻ group of the compound of the formula (IV), any one of the groups referred to above as protecting groups for the carboxyl group of the compound of the formula (II) may be used. On the other hand, any one of the groups mentioned above as protecting groups for the amino group of the compound of the formula (II) may be used as the protecting group for the amino group of the compound of the formula (V). After the reaction, these protecting groups may be removed by using a conventional method such as hydrolysis or reduction in accordance with the kinds of the protecting groups employed.

As the salts of the compounds of the formulae (IV) and (V), suitable salts may be chosen from those described above as the salts of the compounds of formulae (II) and (III).

Acute toxicity [$LD_{50}$ (mouse, intravenous injection)] of the following compounds was more than 3 g/kg, respectively.

7β-[2-(5-Amino-1,2,4-thiadiazol-3-yl)-(Z)-2-fluoromethoxyiminoacetamido]-3-(4-carbamoyl-1-quinuclidinio) methyl-3-cephem-4-carboxylate;

7β-[2-(5-Amino-1,2,4-thiadiazol-3-yl)-(Z)-2-fluoromethoxyiminoacetamido]-3-(4-hydroxy-1,4-methylene-1-piperidinio)methyl-3-cephem-4-carboxylate; and 7β-[2-(5-Amino-1,2,4-thiadiazol-3-yl)-(Z)-2-fluoromethoxyiminoacetamido]-3-(4-hydroxymethyl-1-quinuclidinio)methyl-3-cephem-4-carboxylate.

When using the compounds of this invention as injections, they may be administered generally at a daily dose of 100 mg–10 g in 1–4 portions either intravenously or intramuscularly. Needless to say, the dose may be increased or decreased depending on the age and conditions of disease of the patients.

Their injections may be produced by a method known per se in the art. For example, each compound of this invention may be formulated into an injection by dissolving the same in distilled water, if necessary, in the presence of an isotonic agent, solubilizer and/or the like. They may each be filled as powder in a vial or the like, thereby providing injections which require dissolution before use. These injections are hence dissolved in distilled water for injection, physiological saline, glucose injection, amino acid infusion or the like upon administration.

The present invention will next be described in further detail by the following Experiments and Examples.

EXPERIMENT 1

(Synthesis of Starting Compound)

Ethyl 2-(5-tritylamino-1,2,4-thiadiazol-3-yl)-(Z)-2-fluoromethoxyiminoacetate

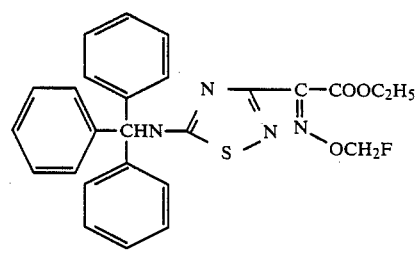

Ethyl 2-(5-tritylamino-1,2,4-thiadiazol-3-yl)-(Z)-2-hydroxyiminoacetate (60.4 g) was dissolved in dimethylsulfoxide (210 ml), followed by an addition of potassium carbonate (96.48 g) under ice-cooling. The resulting mixture was stirred for 10 minutes. Bromofluoromethane (19 g) was thereafter added, followed by stirring at room temperature for 3 hours. Ethyl acetate (1 l) was added to the reaction mixture. The resulting mixture was washed with water and then with saturated saline, and was added with anhydrous magnesium sulfate to dry the mixture. The solvent was distilled out and ethanol (120 ml) was added to the residue. Crystals thus precipitated were collected by filtration and then washed to obtain 58.2 g of the title compound.

EXPERIMENT 2

(Synthesis of Starting Compound)

2-(5-Tritylamino-1,2,4-thiadiazol-3-yl)-(Z)-2-fluoromethoxyiminoacetic acid

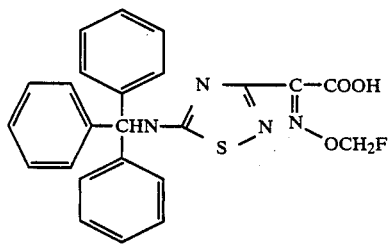

The compound (17.87 g) of Experiment 1 was added to a liquid mixture of sodium hydroxide (2.04 g), ethanol (146 ml) and water (29 ml). Under reflux, the resulting mixture was stirred for 20 minutes. After concentrating the reaction mixture under reduced pressure, ethyl acetate (200 ml) and 1N hydrochloric acid (77 ml) were added. The ethyl acetate layer was separated, washed with saturated saline, and then added with anhydrous magnesium sulfate to dry same. The solvent was distilled off to obtain crystals. Petroleum ether was added to the crystals. The resulting mixture was ground and filtered, thereby obtaining 16.55 g of the title compound.

EXPERIMENT 3

(Synthesis of Starting Compound)

p-Methoxybenzyl 7β-[2-(5-tritylamino-1,2,4-thiadiazol-3-yl)-(Z)-2-fluoromethoxyiminoacetamido]-3-chloromethyl-3-cephem-4-carboxylate

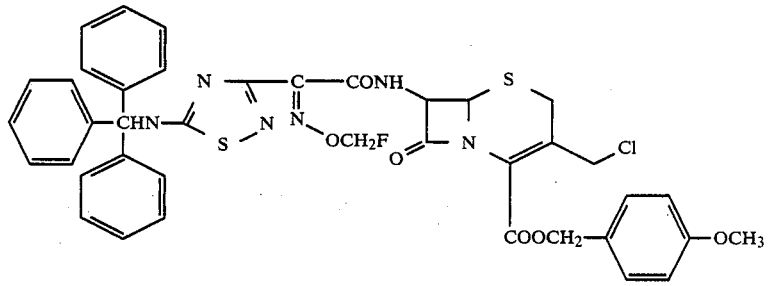

A mixture of dimethylformamide (200 μl) and tetrahydrofuran (4.1 ml) was cooled to −10° C., followed by an addition of phosphorus oxychloride (242 μl). The resulting mixture was stirred for 90 minutes under ice-cooling. A tetrahydrofuran solution (5.5 ml) of the compound (1.00 g) of Experiment 2 was cooled to −10° C. and added to the liquid mixture. The resulting mixture was stirred for 90 minutes under ice-cooling. The reaction mixture was cooled to −20° C., followed by an addition of a liquid mixture of p-methoxybenzyl 7β-amino-3-chloromethyl-3-cephem-4-carboxylate hydrochloride (0.92 g), N-(trimethylsilyl)acetamide (1.42 g) and acetonitrile (10 ml). The resulting mixture was stirred at −10° C. for 1 hour. The reaction mixture was added with ethyl acetate (50 ml), was washed successively with water, a saturated aqueous solution of sodium hydrogencarbonate and saturated saline, and was then added with anhydrous magnesium sulfate to dry same. The solvent was distilled off and the residue was purified by chromatography on a silica gel column, thereby obtaining 1.74 g of the title compound.

EXPERIMENT 4

(Synthesis of Starting Compound)

p-Methoxybenzyl 7β-[2-(5-tritylamino-1,2,4-thiadiazol-3-yl)-(Z)-2-fluoromethoxyiminoacetamido]-3-iodomethyl-3-cephem-4-carboxylate

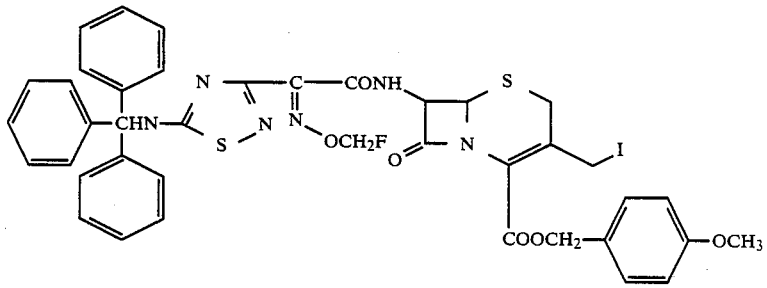

The compound (16.3 g) of Experiment 3 was dissolved in 2-butanone (363 ml), followed by an addition of sodium iodide (12.3 g) under ice-cooling. The resulting mixture was stirred for 15 minutes under ice-cooling and then for 90 minutes at room temperature. The solvent was distilled off and the residue was extracted with ethyl acetate (500 ml). The extract was washed with a saturated aqueous solution of sodium thiosulfate and saturated saline, and was then added with anhydrous magnesium sulfate to dry same. The resulting solution was concentrated under reduced pressure, followed by an addition of n-hexane. A precipitate thus formed was collected by filtration, thereby obtaining 17.6 g of the title compound.

EXPERIMENT 5

(Synthesis of Starting Compound)

Ethyl 2-(5-amino-1,2,4-thiadiazol-3-yl)-(Z)-2-fluoromethoxyiminoacetate

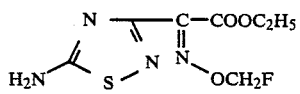

The compound (2.00 g) of Experiment 1 was stirred at room temperature for 30 minutes in trifluoroacetic acid. The solvent was distilled off, and the residue was purified by chromatography on a silica gel to obtain 405 mg of the title compound.

EXPERIMENT 6

(Synthesis of Starting Compound)

2-(5-Amino-1,2,4-thiadiazol-3-yl)-(Z)-2-fluoromethoxyiminoacetic acid

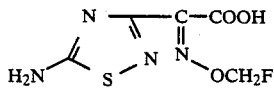

The compound (200 mg) of Experiment 5 was suspended in a mixed solvent of ethanol (6 ml) and water (2 ml). The suspension was added with 1.75 ml of a 1N aqueous solution of sodium hydroxide, followed by stirring at 60° C. for 1 hour. The ethanol was distilled off from the reaction mixture and the resulting solution was adjusted to pH 2 with 1N hydrochloric acid. The thus-adjusted solution was purified on "DIAION SP207" (trade name for non-ionic adsorbent resin; product of Mitsubishi Chemical Industries, Ltd.), thereby obtaining 30 mg of the title compound.

EXPERIMENT 7

(Synthesis of Starting Compound)

7β-[2-(5-Amino-1,2,4-thiadiazol-3-yl)-(Z)-2-fluoromethoxyiminoacetamido]-3-acetoxymethyl-3-cephem-4-carboxylic acid trifluoroacetate

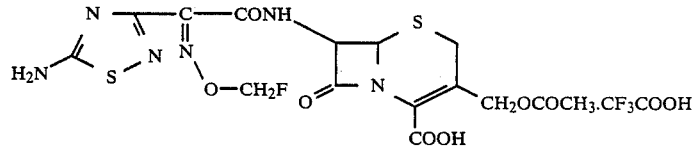

Stirred for 2 hours was a liquid mixture of the compound (10 g) of Experiment 6, t-butyl 7β-amino-3-acetoxymethyl-3-cephem-4-carboxylate (7.4 g), 1-hydroxybenzotriazole (3.1 g), N,N'-dicyclohexylcarbodiimide (4.7 g) and dimethylformamide (100 ml). Ethyl acetate (300 ml) was added to the reaction mixture. A precipitate thus formed was filtered. The filtrate was washed with water and then dried with anhydrous magnesium sulfate. The solution was concentrated under reduced pressure and then purified by chromatography on a silica gel column to obtain 10 g of t-butyl 7β-[2-(5-tritylamino-1,2,4-thiadiazol-3-yl)-(Z)-2-fluoromethoxyiminoacetamido]-3-acetoxymethyl-3-cephem-4-carboxylate. Anisole (50 ml) and trifluoroacetic acid (50 ml) were added to the compound and the resulting mixture was stirred for 3 hours. Isopropyl ether (500 ml) was added to the resulting solution. A precipitate thus formed was filtered to obtain 7.14 g of the title compound.

EXAMPLE 1

7β-[2-(5-Amino-1,2,4-thiadiazol-3-yl)-(Z)-2-fluoromethoxyiminoacetamido]-3-(4-carbamoyl-1-quinuclidinio)methyl-3-cephem-4-carboxylate

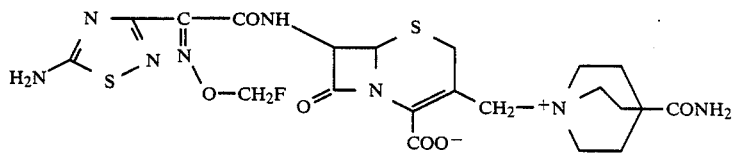

(A) A liquid mixture of the compound (500 mg) of Experiment 6, phosphorus pentachloride (710 mg) and dichloromethane (10 ml) was stirred at −10° C. for 20 minutes. Diisopropyl ether (15 ml) was added to the reaction mixture, and crystals thus formed were collected by filtration to obtain 185 mg of 2-(5-amino-1,2,4-thiadiazol-3-yl)-(Z)-2-fluoromethoxyiminoacetyl chloride hydrochloride.

(B) 7β-Amino-3-(4-carbamoyl-1-quinuclidinio)methyl-3-cephem-4-carboxylate hydrochloride (270 mg) was suspended in a mixed solvent of water (1.5 ml) and methanol (8 ml), followed by an addition of sodium acetate trihydrate (458 mg). The resulting mixture was stirred to dissolve the sodium acetate trihydrate. The acid chloride hydrochloride (185 mg) obtained in the above procedure (A) was added to the resulting solution, followed by stirring for 1 hour. Methanol (8 ml) was added and an insoluble matter was filtered off. After concentrating the filtrate under reduced pressure, the residue was purified by reversed-phase chromatography on a silica gel column to obtain 154 mg of the title compound.

EXAMPLE 2

7β-[2-(5-Amino-1,2,4-thiadiazol-3-yl)-(Z)-2-fluoromethoxyiminoacetamido]-3-(4-methyl-1-quinuclidinio)-methyl-3-cephem-4-carboxylate

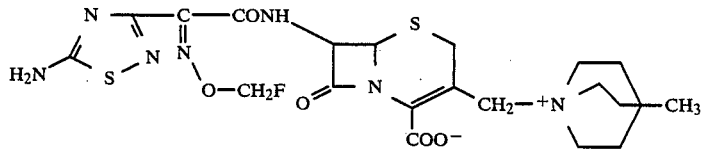

The compound (500 mg) of Experiment 4 was suspended in a mixed solvent of ethyl acetate (20 ml) and ethyl ether (40 ml). Under ice-cooling, 4-methylquinuclidine (63.5 mg) was added and the resulting mixture was stirred for 1 hour. A precipitate thus formed was collected by filtration, washed with isopropyl ether, and then dried to obtain 460 mg of yellow powder.

The yellow powder was added with anisole (2.8 ml) and trifluoroacetic acid (3.2 ml), followed by stirring for 1 hour under ice-cooling. Isopropyl ether was added to the reaction mixture, and a precipitate thus formed was collected by filtration. The precipitate was added with water and an insoluble matter was filtered off. The filtrate was purified by reversed-phase chromatography on a silica gel column to obtain 20 mg of the title compound.

EXAMPLE 3

7β-[2-(5-Amino-1,2,4-thiadiazol-3-yl)-(Z)-2-fluoromethoxyiminoacetamido]-3-(4-hydroxy-1,4-methylene-1-piperidinio)methyl-3-cephem-4-carboxylate

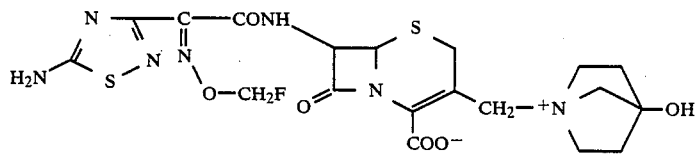

The compound (500 mg) of Experiment 4 was suspended in a mixed solvent of ethyl acetate (25 ml) and ethyl ether (50 ml). Under ice-cooling, 4-hydroxy-1,4-methylenepiperidine (83 mg) was added and the resulting mixture was stirred for 1 hour. A precipitate thus formed was collected by filtration, washed with isopropyl ether, and then dried to obtain 380 mg of yellow powder.

The yellow powder was added with anisole (2.4 ml) and trifluoroacetic acid (2.6 ml), followed by stirring for 1 hour under ice-cooling. Isopropyl ether was added to the reaction mixture, and a precipitate thus formed was collected by filtration. The precipitate was added with water and an insoluble matter was filtered off. The filtrate was purified by reversed-phase chromatography on a silica gel column to obtain 13 mg of the title compound.

Similarly to Examples 2 and 3, the compounds of the following Examples 4–7 were obtained.

EXAMPLE 4

7β-[2-(5-Amino-1,2,4-thiadiazol-3-yl)-(Z)-2-fluoromethoxyiminoacetamido]-3-(1-methyl-1-pyrrolidinio)-methyl-3-cephem-4-carboxylate

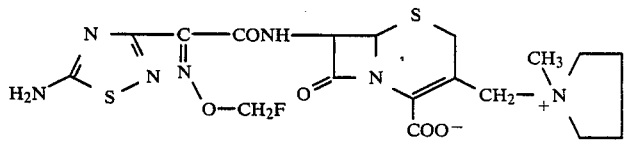

The compound (320 mg) of Experiment 4 and 1-methylpyrrolidine (46 mg) were reacted and the protecting groups were then removed to obtain 6 mg of the title compound.

EXAMPLE 5

7β-[2-(5-Amino-1,2,4-thiadiazol-3-yl)-(Z)-2-fluoromethoxyiminoacetamido]-3-[N,N-dimethyl-N-(2-carbamoyl)ethylammonio]methyl-3-cephem-4-carboxylate

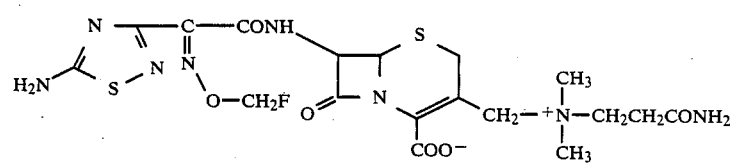

The compound (670 mg) of Experiment 4 and 3-dimethylaminopropionamide (89 mg) were reacted and the protecting groups were then removed to obtain 7 mg of the title compound.

EXAMPLE 6

7β-[2-(5-Amino-1,2,4-thiadiazol-3-yl)-(Z)-2-fluoromethoxyiminoacetamido]-3-(4-carbamoyl-1-methyl-1,2,3,6-tetrahydropyridinio)methyl-3-cephem-4-carboxylate

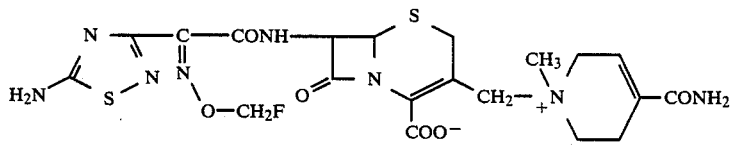

The compound (500 mg) of Experiment 4 and 4-carbamoyl-1-methyl-1,2,3,6-tetrahydropyridine (103 mg) were reacted and the protecting groups were removed to obtain 20 mg of the title compound.

EXAMPLE 7

7β-[2-(5-Amino-1,2,4-thiadiazol-3-yl)-(Z)-2-fluoromethoxyiminoacetamido]-3-[tris(2-hydroxyethyl)ammonio]methyl-3-cephem-4-carboxylate

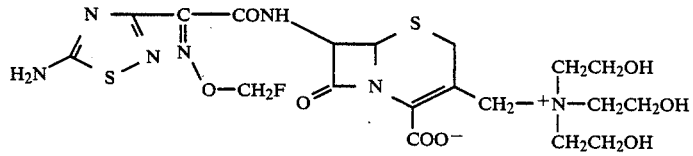

The compound (2.0 g) of Experiment 4 and triethanolamine (270 mg) were reacted and the protecting groups were removed to obtain 6 mg of the title compound.

EXAMPLE 8

7β-[2-(5-Amino-1,2,4-thiadiazol-3-yl)-(Z)-2-fluoromethoxyiminoacetamido]-3-[1-morpholino-[4,3-b]pyrazolio]methyl-3-cephem-4-carboxylate

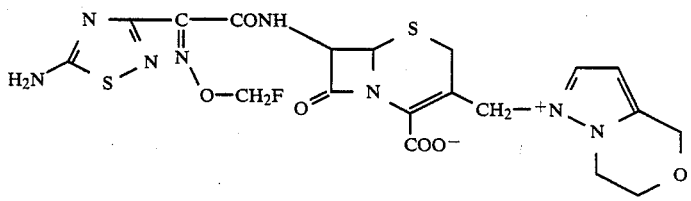

Stirred at 60° C. for 3 hours was a mixture composed of the compound (500 mg) of Experiment 7, morpholino[4,3-b]pyrazole (500 mg), sodium iodide (2.0 g) and water (1.5 ml). Acetone (50 ml) was added to the reaction mixture, and a precipitate thus formed was collected by filtration. The precipitate was purified by reversed-phase chromatography on a silica gel column to obtain 53 mg of the title compound.

Similarly to Example 8, the compounds of the following Examples 9 and 10 were synthesized.

EXAMPLE 9

7β-[2-(5-Amino-1,2,4-thiadiazol-3-yl)-(Z)-2-fluoromethoxyiminoacetamido]-3-[2-(2-hydroxyethyl)-1-pyrazolio]methyl-3-cephem-4-carboxylate

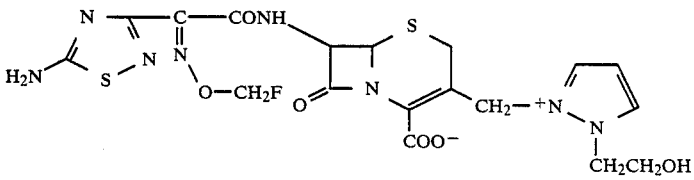

The compound (400 mg) of Experiment 7 and 1-(2-hydroxyethyl)pyrazole (400 mg) were reacted to obtain 50 mg of the title compound.

EXAMPLE 10

7β-[2-(5-Amino-1,2,4-thiadiazol-3-yl)-(Z)-2-fluoromethoxyiminoacetamido]-3-[1-(2,3-tetramethylene)-pyrazolio]methyl-3-cephem-4-carboxylate

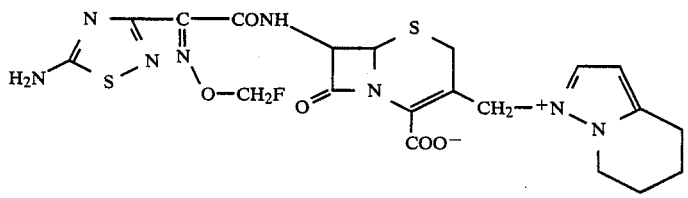

The compound (500 mg) of Experiment 7 and 1,5-tetramethylenepyrazole (500 mg) were reacted to obtain 15 mg of the title compound.

EXAMPLE 11

7β-[2-(5-Amino-1,2,4-thiadiazol-3-yl)-(Z)-2-fluoromethoxyiminoacetamido]-3-(4-hydroxylmethyl-1-quinuclidinio)methyl-3-cephem-4-carboxylate

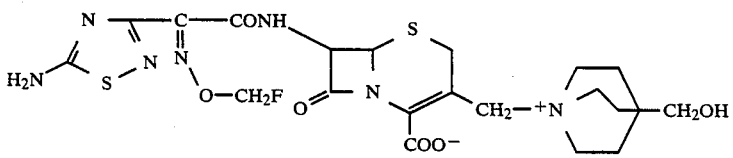

The compound (1.0 g) of Experiment 4 was dissolved in a mixed solution of ethyl acetate (70 ml) and isopropyl ether (30 ml).

Hydroxymethyl quinuclidine (134 mg) was dissolved in a mixed solution of ethyl acetate (10 ml) and methanol (1 ml).

Under ice-cooling, the latter solution was added dropwise to the former solution for 50 minutes. The mixture was stirred for 30 minutes at the same temperature. A precipitate thus formed was collected by filtration, and washed with isopropyl ether, to obtain 837 mg of yellow powder.

The yellow powder was added with anisole (6 ml) and trifluoroacetic acid (10 ml), followed by stirring for 30 minutes under ice-cooling. Isopropyl ether was added to the reaction mixture, and a precipitate thus formed was collected by filtration. The precipitate was added with a water-methanol mixture, and the whole was adjusted under ice-cooling to pH 5.4 with an aqueous solution of sodium acetate. Methanol is distilled off, followed by purifying the residue by reversed-phase chromatography on a silica gel column to obtain 125 mg of the title compound.

TABLE 1

List of physical data

| | Infrared absorption spectrum (cm$^{-1}$, Nujol) | NMR Spectrum (δ) |
|---|---|---|
| Experiment No. | | |
| 1 | 1735, 1530 | (DMSO-d$_6$) 1.19 (3H, t, J = 7 Hz), 4.21 (2H, q, J = 7 Hz), 5.79 (2H, d, J = 55 Hz), 7.30 (15H, s), 10.03 (1H, s) |
| 2 | 1720, 1585 | (DMSO-d$_6$) 5.78 (2H, d, J = 55 Hz), 7.31 (15H, s), 10.06 (1H, s) |
| 3 | — | (CDCl$_3$) 3.55 (2H, m), 3.80 (3H, s), 4.43 (1H, d, J = 14.5 Hz), 4.56 (1H, d, J = 14.5 Hz), 5.04 (1H, d, J = 5 Hz), 5.21 (2H, s), 5.83 (2H, d, J = 55 Hz), 5.94 (1H, m), 6.89 (2H, d, J = 9 Hz), 7.16~7.50 (17H, m), 7.71 (1H, s) |
| 4 | — | (CDCl$_3$) 3.53 (2H, m), 3.78 (3H, s), 4.32 (2H, b), 5.97 (1H, d, J = 5 Hz), 5.16 (2H, s), 5.76 (1H, d, J = 54 Hz), 5.82 (1H, dd, J = 9 Hz, 5 Hz), 6.81 (2H, d, J = 9 Hz), 7.0~7.4 (17H, m), 7.63 (1H, s) |
| 5 | 1730, 1615 | (DMSO-d$_6$) 1.28 (3H, t, J = 7.0 Hz), 4.34 (2H, q, J = 7.0 Hz), 5.83 (2H, d, J = 54.5 Hz), 8.27 (2H, brs) |
| 6 | 1720, 1620 | (DMSO-d$_6$) 5.76 (2H, d, J = 55.8 Hz), 8.12 (2H, brs) |
| 7 | 1770, 1710, 1670, 1610 | (DMSO-d$_6$) 2.02 (3H, s), 3.45 (1H, d, J = 10 Hz), 3.80 (1H, d, J = 10 Hz), 4.63 (2H, d, J = 17 Hz), 4.96 (1H, d, J = 17 Hz), 5.13 (1H, d, J = 5 Hz), 5.67 (2H, d, J = 60 Hz), 5.78 (1H, dd, J = 5 Hz, 10 |
| Example No. | | |
| 1 | 1770 | (D$_2$O) 2.27 (6H, m), 3.3~4.2 (m), 5.43 (1H, d, J = 5 Hz), 5.97 (1H, d, J = 5 Hz), 5.92 (2H, d, J = 54 Hz) |
| 2 | 1770 | (D$_2$O) 1.03 (3H, s), 1.82 (6H, b), 3.10~4.10 (10H, m), 5.36 (1H, d, J = 5 Hz), 5.84 (1H, d, J = 54 Hz), 5.89 (1H, d, J = 5 Hz) |
| 3 | 1770 | (D$_2$O) 2.25 (4H, m), 3.2~4.4 (10H, m), 5.40 (1H, d, J = 5 Hz), 5.90 (2H, d, J = 54 Hz), 5.95 (1H, d, J = 5 Hz) |
| 4 | 1770 | (D$_2$O) 2.26 (4H, m), 3.02 (3H, s), 3.3~4.1 (8H, m), 5.38 (1H, d, J = 5 Hz), 5.85 (2H, d, J = 54 Hz), 5.90 (1H, d, J = 5 Hz) |
| 5 | 1770 | (D$_2$O) 2.70~3.18 (4H), 3.05 (3H, s), 3.11 (3H, s), 3.50~4.10 (4H, m), |

TABLE 1-continued

List of physical data

| | Infrared absorption spectrum (cm$^{-1}$, Nujol) | NMR Spectrum ($\delta$) |
|---|---|---|
| 6 | 1770 | 5.38 (1H, d, J = 5 Hz), 5.86 (2H, d, J = 54 Hz), 5.90 (1H, d, J = 5 Hz) (D$_2$O) 2.78 (2H, b), 3.04, 3.12 ( 3H, S 2 ), 3.23~4.3 (8H, m), |
| 7 | 1770 | 5.38 (1H, d, J = 5 Hz), 5.90 (1H, d, J = 5 Hz), 5.87 (2H, d, J = 54 Hz), 6.38~6.66 (1H, m) (D$_2$O) 3.56 (6H, m), 3.96 (6H, m), 5.23 (1H, d, J = 5 Hz), 5.73 (2H, d, J = 54 Hz), 5.78 (1H, d, J = 5 Hz) |
| 8 | 1770, 1670, 1610 | (D$_2$O) 3.35 (1H, d, J = 18 Hz), 3.61 (1H, d, J = 18 Hz), 4.25~4.5 (4H, m), 5.13 (2H, s), 5.37 (1H, d, J = 15.4 Hz), 5.37 (1H, d, J = 5.1 Hz), 5.55 (1H, d, J = 15.4 Hz), 5.95 (2H, d, J = 45.6 Hz), 5.99 (1H, d, J = 5.1 Hz), 6.78 (1H, d, J = 2.9 Hz), 8.52 (1H, d, J = 29 Hz) |
| 9 | 1770, 1670, 1610 | (DMSO-d$_6$) 3.3~3.6 (2H, m), 3.7~3.8 (2H, m), 4.65~4.75 (2H, m), 5.05 (1H, d, J = 4.6 Hz), 5.42 (1H, d, J = 15 Hz), 5.52 (1H, d, J = 15 Hz), 5.65~5.70 (1H, m), 5.75 (2H, d, J = 57.2 Hz), 6.90 (1H, t, J = 2.9 Hz), 8.48 (1H, d, J = 2.5 Hz), 8.56 (1H, d, J = 2.5 Hz) |
| 10 | 1765, 1665, 1600 | (D$_2$O) 1.9~2.05 (2H, m), 2.2~2.35 (2H, m), 3.07 (2H, t, J = 5.0 Hz), 3.33 (1H, d, J = 17.6 Hz), 3.56 (1H, d, J = 17.6 Hz), 4.2~4.5 (2H, m), 5.28 (1H, d, J = 15.3 Hz), 5.35 (1H, d, J = 4.7 Hz), 5.53 (1H, d, J = 15.3 Hz), 5.96 (2H, d, J = 54.6 Hz), 6.00 (1H, d, J = 4.7 Hz), 6.68 (1H, d, J = 2.5 Hz), 8.18 (1H, d, J = 2.5 Hz) |
| 11 | 1770 | (CD$_3$COCD$_3$—D$_2$O) 1.82 (6H, m), 3.2~4.0 (m), 4.75 (1H, d, J = 13 Hz), 5.27 (1H, d, H = 5 Hz), 5.76 (2H, d, J = 54 Hz), 5.83 (1H, d, J = 5 Hz) |

TABLE 2

Effect of the Invention
List of anti-bacterial activity

Test bacterium MIC ($\mu$g/ml) Inoculum size 10$^6$ CFU/ml

| Test compound | Staph. aureus 209-P | Escher. coli NIHJ | Kleb. pneumoniae EK-6 | Ser. marcescens ES-75 | Morganella morganii EP-14 | Pseud. aeruginosa EP-01 |
|---|---|---|---|---|---|---|
| Example | | | | | | |
| 1 | 1.56 | 0.05 | 0.05 | 0.1 | 0.05 | 0.4 |
| 2 | 0.8 | 0.05 | 0.05 | 0.1 | 0.1 | 0.8 |
| 3 | 0.4 | 0.05 | 0.1 | 0.1 | 0.05 | 0.8 |
| 4 | 0.8 | ≦0.025 | 0.05 | 0.05 | ≦0.025 | 0.8 |
| 5 | 1.56 | ≦0.025 | ≦0.025 | 0.1 | 0.05 | 1.56 |
| 6 | 1.56 | 0.05 | 0.05 | 0.1 | 0.05 | 0.8 |
| 7 | 6.25 | 0.1 | 0.1 | 0.4 | 0.1 | 3.13 |
| 8 | 0.4 | ≦0.025 | 0.05 | 0.05 | 0.05 | 0.8 |
| 9 | 0.4 | 0.05 | 0.05 | 0.05 | 0.05 | 0.8 |
| 10 | 0.4 | ≦0.025 | ≦0.025 | 0.05 | 0.05 | 0.8 |
| 11 | 0.8 | ≦0.025 | ≦0.025 | 0.1 | ≦0.025 | 0.4 |

What is claimed is:

1. A thiadiazolylacetamide cephem compound of the formula:

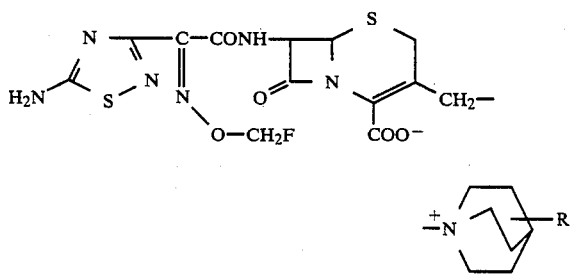

or a pharmaceutically acceptable salt thereof, wherein R is carbamoyl or hydroxy lower alkyl.

2. An antibacterial composition, which comprises an antibacterially effective amount of a thiadiazolylacetamide cephem compound according to claim 1, and a pharmaceutically acceptable carrier therefor.

3. A method of treating a bacterial infection in a mammal, which comprises administering to said mammal in need of treatment an antibacterially effective amount of a thiadiazolylacetamide cephem compound according to claim 1.

4. The compound as claimed in claim 1, which is 7$\beta$-[2-(5-amino-1,2,4-thiadiazol-3-yl)-(Z)-2-fluoromethoxyiminoacetamido]-3-(4-carbamoyl-1-quinuclidinio)methyl-3-cephem-4-carboxylate.

5. The compound as claimed in claim 1, which is 7$\beta$-[2-(5-amino-1,2,4-thiadiazol-3-yl)-(Z)-2-fluoromethoxyiminoacetamido]-3-(4-hydroxymethyl-1-quinuclidinio)methyl-3-cephem-4-carboxylate.

* * * * *